United States Patent [19]

Siegrist et al.

[11] 4,113,937
[45] Sep. 12, 1978

[54] STILBENE COMPOUNDS

[75] Inventors: Adolf Emil Siegrist, Basel; Jean-Paul Pauchard, Fribourg, both of Switzerland

[73] Assignee: Ciba-Geigy Corporation, Ardsley, N.Y.

[21] Appl. No.: 850,861

[22] Filed: Nov. 14, 1977

[30] Foreign Application Priority Data

Nov. 25, 1977 [LU] Luxembourg ............... 77024

[51] Int. Cl.² .......................................... C09B 23/00
[52] U.S. Cl. ..................... 542/463; 542/462; 252/301.24; 252/301.27; 252/301.28; 252/301.29
[58] Field of Search .................... 542/462, 463

[56] References Cited

U.S. PATENT DOCUMENTS

| | | | |
|---|---|---|---|
| 3,277,102 | 10/1966 | Buell et al. ................... | 542/463 X |
| 3,732,221 | 5/1973 | Siegrist et al. ............... | 542/462 X |
| 3,817,990 | 6/1974 | Strobel et al. ................ | 542/463 |
| 3,871,898 | 3/1975 | Reinert et al. ................ | 542/463 X |
| 4,039,531 | 8/1977 | Günther et al. ............... | 542/462 |

*Primary Examiner*—Paul F. Shaver
*Attorney, Agent, or Firm*—Edward McC. Roberts; Prabodh I. Almaula

[57] ABSTRACT

Novel stilbene compounds of the formula

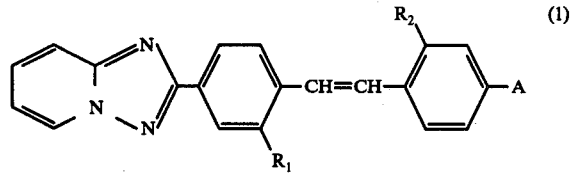

in which $R_1$ and $R_2$ independently of one another are hydrogen or chlorine and A is a mono-nuclear or polynuclear aromatic heterocyclic structure which contains oxygen atoms or oxygen and nitrogen atoms and is unsubstituted or substituted by non-chromophoric substituents, as well as their use in a process for optically brightening organic material are disclosed.

9 Claims, No Drawings

STILBENE COMPOUNDS

The present application relates to novel stilbene compounds and a process for their preparation and to processes for the optical brightening of organic materials by means of these novel stilbene compounds.

The stilbene compounds according to the invention are of the formula

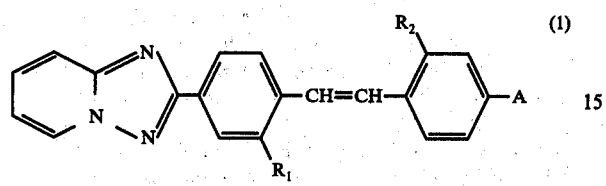

in which $R_1$ and $R_2$ independently of one another are hydrogen or chlorine and A is a mono-nuclear or polynuclear aromatic heterocyclic structure which contains oxygen atoms or oxygen and nitrogen atoms and is unsubstituted or substituted by non-chromophoric substituents.

Examples of possible mono-nuclear or poly-nuclear aromatic heterocyclic structures which contain oxygen atoms or oxygen and nitrogen atoms are benzofuran, benzoxazole, isoxazole, 1,2,4-oxadiazole, 1,3,4-oxadiazole, (1-naphthyl)-1,3,4-oxadiazole and (2-naphthyl)-1,3,4-oxadiazole radicals and these can be unsubstituted or substituted by non-chromophoric substituents.

Non-chromophoric substituents of such heterocyclic structures are, for example, substituted or unsubstituted alkyl having 1 to 8 C atoms, halogen, substituted or unsubstituted phenyl, substituted or unsubstituted alkoxy having 1 to 4 C atoms, phenoxy, carboxyl, carbalkoxy having 1 to 4 C atoms in the alkoxy part, cyano, benzyl or sulpho. Carboxy and sulpho substituents can also be in the form of alkali metal salts or amine salts or in the form of functional derivatives, for example in the form of esters.

"Halogen" is to be understood as meaning chlorine, bromine and fluorine and especially chlorine.

Within the scope of the formula (1), compounds of interest are, in particular, those of the formula

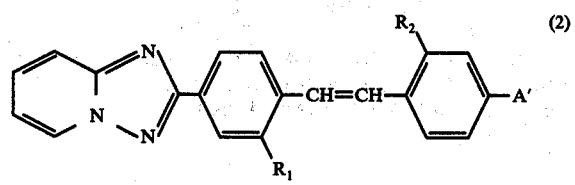

in which $R_1$ and $R_2$ are as defined above and A' is a benzo[b]furan-2-yl, benzoxazol-2-yl, 3-phenyl-isoxazol-5-yl, 3-phenyl-1,2,4-oxadiazol-5-yl, 5-phenyl-1,3,4-oxadiazol-2-yl, 5-(1-naphthyl)-1,3,4-oxadiazol-2-yl or 5-(2-naphthyl)-1,3,4-oxadiazol-2-yl radicals which is unsubstituted or substituted by non-chromophoric substituents.

Preferred compounds are the stilbene compounds of the formula

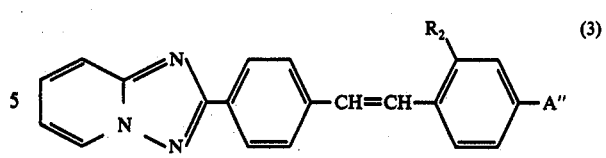

in which $R_2$ is hydrogen or chlorine and A" is a radical of the formula

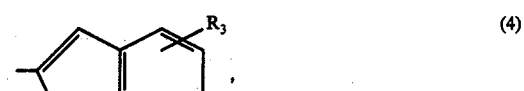

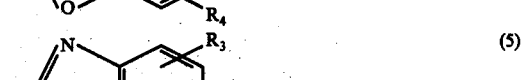

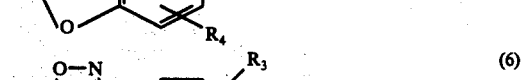

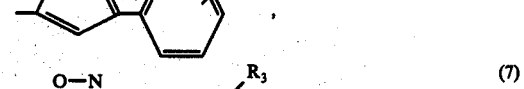

or

in which $R_3$ is hydrogen, halogen, alkyl having 1 to 4 C atoms, alkoxy having 1 to 4 C atoms, cyclohexyl, phenyl or phenylalkyl having 1 to 4 C atoms in the alkyl part, or $R_3$ together with $R_5$ is the complement to a 1-naphthyl or 2-naphthyl radical, $R_4$ is hydrogen or alkyl having 1 to 4 C atoms and $R_5$ is hydrogen or, together with $R_3$, is the complement to a 1-naphthyl or 2-naphthyl radical.

Compounds of interest in practice are the stilbene compounds of the formula

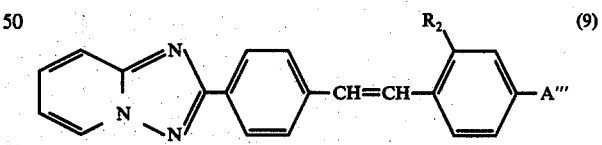

in which $R_2$ is hydrogen or chlorine and A''' is a radical of the formula

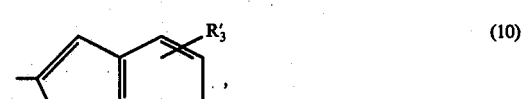

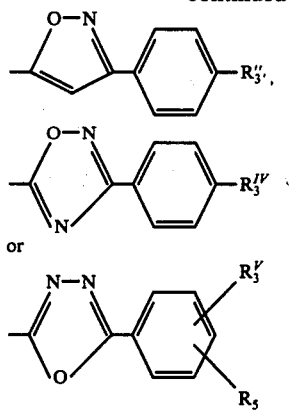

in which $R_3'$ is hydrogen, chlorine, methyl, methoxy or phenyl, $R_4'$ is hydrogen or methyl, $R_3''$ is hydrogen, chlorine, alkyl having 1 to 4 C atoms, methoxy, phenyl, benzyl or cyclohexyl, $R_4$ is hydrogen or alkyl having 1 to 4 C atoms, $R_3'''$ is hydrogen, chlorine, methoxy or phenyl, $R_3^{iv}$ is hydrogen, chlorine, methoxy, alkyl having 1 to 4 C atoms or phenyl, $R_3^v$ is hydrogen, chlorine, alkyl having 1 to 4 C atoms, methoxy or phenyl or, together with $R_5$ is the complement to a 1-naphthyl or 2-naphthyl radical, and $R_5$ is hydrogen or, together with $R_3'$, is the complement to a 1-naphthyl or 2-naphthyl radical, and especially those of the formula (9) in which $A'''$ is a radical of the formula (11), (13) or (14).

The stilbene compounds according to the invention can be prepared by various processes. Thus, the compounds of the formula (1) can be prepared by reacting a Schiff's base of the formula

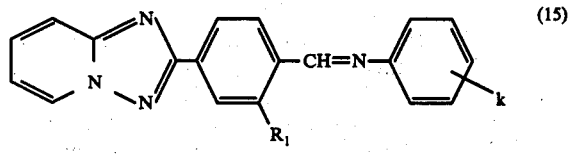

in which $k$ is hydrogen or chlorine and $R_1$ is as defined above, with a methyl compound of the formula

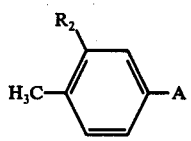

in which $R_2$ and A are as defined above, in dimethylformamide and in the presence of a strongly basic alkali metal compound.

Compounds used as the strongly basic alkali metal compound are, depending on the reactivity of the Schiff's base (anil) employed, alkali metal compounds of the formula $$YOC_{m-1}H_{2m-1} \qquad (17)$$

in which $m$ is an integer from 1 to 6 and preferably 2 to 6 and Y is an alkali metal ion, preferably sodium or potassium, for example potassium hydroxide or, especially, potassium tertiary butylate. In the case of alkali metal alcoholates, the reaction must be carried out in a virtually anhydrous medium, whilst in the case of potassium hydroxide a low water content of up to about 15% (for example content of water of crystallisation) is still permissible.

The compounds containing methyl groups are reacted with the anils in equivalent amounts, i.e., in a molar ratio of 1:1, so that no component is present in a substantial excess. Advantageously, at least the equivalent amount of the alkali metal compound is used, i.e., at least 1 mol of a compound containing, for example, a KO group per mol of aldehyde-anil. When potassium hydroxide is used, preferably the 4-fold to 8-fold amount is employed.

The reaction is carried out at temperatures in the range between about 10° and 50° C. and, if necessary in order to initiate the reaction, with irradiation with additional UV light having a wavelength of more than 300 mm. The use of low temperatures is advantageous if the reactants contain ring compounds or substituents which can easily be opened or, respectively, detached or otherwise chemically changed by alkali. This applies, for example, in the case of anils having easily detachable chlorine substituents. The preparation of the anil and the reaction thereof with the tolyl compound can also be carried out in a one-pot process. For example, the aldehyde is heated with excess aniline in dimethylformamide, the reaction mixture is evaporated completely in vacuo, the tolyl component and dimethylformamide are added and the customary procedure is followed. The end products can be worked up from the reaction mixture by conventional methods which are known per se. Isolation is effected, for example, by precipitation with water or, in the case of water-soluble products, by salting out, for example with NaCl or KCl, or by neutralisation, if appropriate by acidifying with a strong mineral acid, for example HCl.

The starting materials of the formulae (15) and (16) are known or are prepared analogously to processes which are known per se.

The compounds of the formulae (2), (3) and (9) are prepared in an analogous manner by reacting Schiff's bases of the formulae indicated below with methyl compounds of the formulae indicated below:

| For compounds of the formula | Schiff's base | Methyl compound |
|---|---|---|
| (3) | 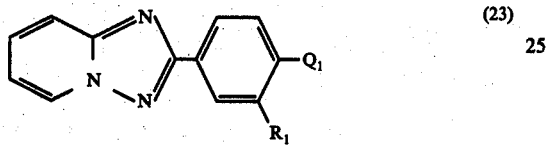 (20) | (22) |
| (9) |  (20) | |

In the formulae (18) to (22), k, $R_1$, $R_2$, A', A" and A'" are as defined above.

The compounds of the formula (1) can also be prepared by reacting one mol equivalent of a compound of the formula

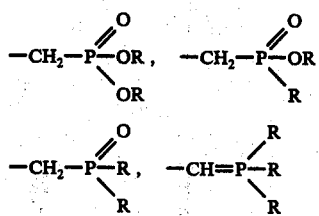
(23)

in which $R_1$ is as defined above, with one mol equivalent of a compound of the formula (24)

in the presence of a strong base and of a solvent, A and $R_2$ being as defined above and one of the symbols $Q_1$ and $Q_2$ being a —CHO group and the other being one of the groupings of the formulae $$-CH_2-P{\overset{O}{\underset{OR}{\parallel}}}OR, \quad -CH_2-P{\overset{O}{\underset{R}{\parallel}}}OR$$

$$-CH_2-P{\overset{O}{\underset{R}{\parallel}}}R, \quad -CH=P{\overset{R}{\underset{R}{\diagup}}}R$$

in which R is an unsubstituted or substituted alkyl, aryl, cycloalkyl or aralkyl radical.

The starting materials of the formulae (23) and (24) are known or can be prepared analogously to processes which are known per se.

The novel compounds defined above exhibit a more or less pronounced fluorescence in the dissolved or finely dispersed state. They can be used for optically brightening the most diverse synthetic, semi-synthetic or natural organic materials or substances which contain such organic materials. The novel compounds have good to very good fastness to light.

The following groups of organic materials, where optical brightening thereof is relevant, may be mentioned as examples of the above, without the survey given below being intended to express any restriction thereto:

I. Synthetic organic high-molecular materials:
a) Polymerisation products based on organic compounds containing at least one polymerisable carbon-carbon double bond, i.e., their homopolymers or copolymers as well as their after-treatment products, for example crosslinking, grafting or degradation products, polymer blends or products obtained by modification of reactive groups, for example polymers based on $\alpha,\beta$-unsaturated carboxylic acids or derivatives of such carboxylic acids, especially on acrylic compounds (for example acrylates, acrylic acid, acrylonitrile, acrylamides and their derivatives or their methacrylic analogues), on olefine hydrocarbons (for example ethylene, propylene, styrenes or dienes and also so-called ABS polymers), and polymers based on vinyl and vinylidene compounds (for example vinyl chloride, vinyl alcohol and vinylidene chloride), b) Polymerisation products which are obtainable by ring opening, for example polyamides of the polycaprolactam type, and also polymers which are obtainable either via polyaddition or via polycondensation, such as polyethers or polyacetals, c) Polycondensation products or precondensates based on bifunctional or polyfunctional compounds possessing groups capable of undergoing condensation reactions, their homocondensation and cocondensation products, and after-treatment products, for example polyesters, especially polyesters which are saturated (for example ethylene glycol terephthalic acid polyesters) or unsaturated (for example maleic acid/dialcohol polycondensates as well as their crosslinking products with copolymerisable vinyl monomers), unbranched or branched polyesters (also including those based on polyhydric alcohols, for example alkyd resins), polyamides (for example hexamethylenediamine adipate), maleate resins, melamine resins, their precondensates and analogues, polycarbonates and silicones, and d) Polyaddition products such as polyurethanes (cross-linked and non-crosslinked) and epoxide resins.

II. Semi-synthetic organic materials, for example cellulose esters of varying degrees of esterification (so-called 2½-acetate or triacetate) or cellulose ethers, regenerated cellulose (viscose or cuprammonium cellulose) or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, i.e., for example, in the form of predominantly three-dimensional bodies, such as slabs, profiles, injection mouldings, various machined articles, chips, granules or foams, and also in the form of predominantly two-dimensional bodies, such as films, sheets, lacquers, coverings, impregnations and coatings, or in the form of predominantly one-dimensional bodies, such as filaments, fibres, flocks and wires. The said materials can, on the other hand, also be in unshaped states, in the most diverse homogeneous or inhomogeneous forms of division, for example in the form of powders, solutions, emulsions, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings or flocked structures or in the form of woven textile fabrics or textile laminates or knitted fabrics and also in the form of papers, cardboards or paper pulps.

The compounds to be used according to the invention are of importance, inter alia, for the treatment of organic textile materials, especially woven textile fabrics. Where fibres, which can be in the form of staple fibres or continuous filaments or in the form of hanks, woven fabrics, knitted fabrics, non-wovens, flocked substrates or laminates, are to be optically brightened according to the invention, this is advantageously effected in an aqueous medium in which the compounds in question are present in a finely divided form (suspensions, so-called micro-dispersions or possibly solutions). If desired, dispersing agents, stabilisers, wetting agents and further auxiliaries can be added during the treatment.

Depending on the type of brightener compound used, it can prove advantageous to carry out the treatment in a neutral or alkaline or acid bath. The treatment is usually carried out at temperatures of about 20° to 140° C., for example at the boiling point of the bath or near it (about 90° C.). Solutions or emulsions in organic solvents can also be used for the finishing, according to the invention, of textile substrates, as is practised in the dyeing trade in so-called solvent dyeing (pad-thermofix application, or exhaustion dye processes in dyeing machines).

The novel optical brighteners according to the present invention can further be added to, or incorporated in, the materials before or during shaping. Thus they can, for example, be added to the compression moulding composition or injection moulding composition during the production of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), i.e., before or during the polymerisation, polycondensation or polyaddition, powdering on to polymer chips or granules for spinning compositions, bath dyeing of polymer chips or granules for spinning compositions, metered addition to spinning melts or spinning solutions, and application to the tow before stretching.

The novel optical brighteners according to the present invention can, for example, also be employed in the following use forms:

a) Mixed with dyestuffs (shading) or pigments (coloured pigments or especially, for example, white pigments), or as an additive to dye baths, printing pastes, discharge pastes or reserve pastes, and also for the after-treatment of dyeings, prints or discharge prints, b) Mixed with so-called "carriers", wetting agents, plasticisers, swelling agents, anti-oxidants, light stabilisers, heat stabilisers and chemical bleaching agents (chlorite bleach or bleaching bath additive), c) Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, anti-soiling finishes or anti-static finishes, or anti-microbial finishes, d) Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather, e) As additives to so-called "master batches", f) As additives to the most diverse industrial products in order to render these more marketable (for example improving the appearance of soaps, washing agents and pigments), g) In combination with other optically brightening substances, h) In spinning bath formulations, i.e., as additives to spinning baths, such as are used for improving the slip for the further processing of synthetic fibres, or from a special bath before stretching the fibre, i) As scintillators for various purposes of a photographic nature, for example for electrophotographic reproduction or supersensitisation, and j) Depending on the substitution, as laser dyes.

If the brightening process is combined with textile treatment methods or finishing methods, the combined treatment can in many cases advantageously be carried out with the aid of appropriate stable formulations which contain the optically brightening compounds in such concentration that the desired brightening effect is achieved.

In certain cases, the brighteners are made fully effective by an after-treatment. This can be, for example, a chemical treatment (for example acid treatment), a thermal treatment (for example heat) or a combined chemical/thermal treatment. Thus, for example, the appropriate procedure to follow in optical brightening a range of fibre substrates, for example polyester fibres, with the brighteners according to the invention, is to impregnate these fibres with the aqueous dispersions (or possibly also solutions) of the brighteners at temperatures below 75° C., for example at room temperature, and to subject them to a dry heat treatment at temperatures above 100° C., it being generally advisable additionally to dry the fibre material beforehand at a moderately elevated temperature, for example at not less than 60° C. and up to about 130° C. The heat treatment in the dry state is then advantageously carried out at temperatures between 120° and 225° C., for example by heating in a drying chamber, by ironing within the specified temperature range or by treatment with dry, superheated steam. The dyeing and dry heat treatment can also be carried out in immediate succession or can be combined in a single process stage.

The amount of the novel optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and in some cases of up to about 2 percent by weight can also be employed. For most practical purposes, amounts between 0.0005 and 0.5 percent by weight are of preferred interest.

For various reasons it is frequently appropriate to employ the brighteners not as such, i.e., in the pure form, but as a mixture with very diverse auxiliaries and diluents, for example anhydrous sodium sulphate, sodium sulphate decahydrate, sodium chloride, sodium carbonate, alkali metal phosphates, such as sodium orthophosphate or potassium orthophosphate, sodium pyrophosphate or potassium pyrophosphate and sodium tripolyphosphates or potassium tripolyphosphates, or alkali metal silicates.

The novel optical brighteners are also especially suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spraydrying, to the washing powder, or to the preparation of liquid washing agent combinations. They can be added either in the form of a solution or dispersion in water or other solvents or, without auxiliaries, as a dry brightener powder. For example, the brighteners can be mixed, kneaded or ground with the detergent substances and, in this form, admixed to the finished washing powder. However, they can also be sprayed in a dissolved or pre-dispersed form on to the finished washing agent.

Possible washing agents are the known mixtures of detergent substances, for example soap in the form of chips and powders, synthetics, soluble salts of sulphonic acid half esters of higher fatty alcohols, arylsulphonic acids with higher and/or multiple alkyl substituents, sulphocarboxylic acid esters of medium to higher alcohols, fatty acid acylaminoalkyl- or acylaminoarylglycerolsulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminetetraacetic acid, and foam stabilisers, such as alkanolamides of higher fatty acids. The washing agents can further contain, for example: anti-static agents, superfatting skin protection agents, such as lanolin, enzymes, anti-microbial agents, perfumes and dyes.

The novel optical brighteners have the particular advantage that they are also effective in the presence of active chlorine donors, for example hydrochlorite, and can be used without significant loss of the effect in wash liquors containing non-ionic washing agents, for example alkylphenol polyglycol ethers.

The compounds according to the invention are added in amounts of 0.005–1% or more, relative to the weight of the liquid or pulverulent, finished washing agent. Wash liquors which contain the indicated amounts of the optical brighteners claimed impart a brilliant appearance in daylight when used to wash textiles of cellulose fibres, polyamide fibres, cellulose fibres with a high quality finish, polyester fibres, wool and the like.

The washing treatment is carried out, for example, as follows:

The textiles quoted are treated for 1 to 30 minutes at 20° to 100° C. in a wash liquor which contains 1 to 10 g/kg of a composite washing agent containing a builder and 0.05 to 1%, relative to the weight of washing agent, of the brighteners claimed. The liquor ratio can be 1:3 to 1:50. After washing, rinsing and drying are carried out as usual. The wash liquor can contain 0.2 g/l of active chlorine (for example as hypochlorite) or 0.1 to 2 g/l of sodium perborate, as a bleaching additive.

In the examples, parts, unless otherwise indicated, are always parts by weight and percentages are always percentages by weight. Unless otherwise noted, melting points and boiling points are uncorrected.

EXAMPLE 1

2.43 g of 2-(p-tolyl)-5-chloro-benzo[b]furane of the formula

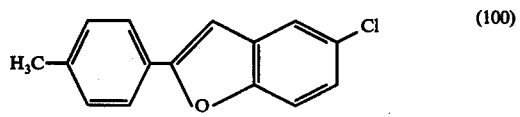

(100)

3.33 g of the Schiff's base obtained from 2-(p-formylphenyl)-s-triazolo[1.5-a]pyridine and o-chloroaniline, of the formula

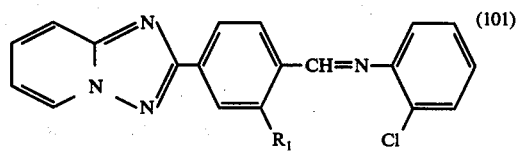

(101)

and 2.24 g of potassium t-butylate are stirred in 80 ml of dimethylformamide for one hour at 25° to 30° C. under nitrogen and during this time the colour of the reaction mixture changes from pale yellow to dark violet. After adding 400 ml of methanol, the mixture is cooled to −10° C. and the product which has precipitated is filtered off with suction, washed with 100 ml of methanol and dried. This gives 2.65 g (59.3% of theory) of 4-[s-triazolo[1,5-a]pyrid-2-yl]-4'-(5-chloro-benzo[b]-furan-2-yl)-stilbene of the formula

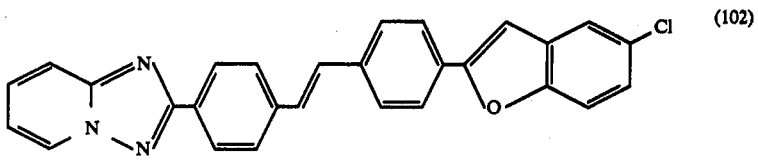

in the form of orange-yellow fine crystals with a melting point of 334° to 336° C. After recrystallisation from o-dichlorobenzene (bleaching earth) and then from dimethylformamide, 1.45 g (32.4% of theory) of greenish-tinged yellow small glossy leaves are obtained which melt at 358° to 359° C.

$C_{28}H_{18}ClN_3O$ (447.92): calculated: C 75.08 H 4.05 N 9.38%: found: C 74.78 H 4.16 N 9.53%.

The compounds of the formula

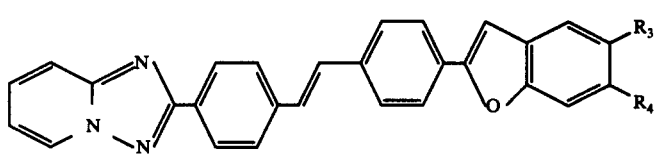

listed in Table I can be prepared in an analogous manner:

TABLE I

| No. | $R_3$ | $R_4$ | Melting point: °C |
|---|---|---|---|
| (104) | H | H | 359–360 |
| (105) | $CH_3$ | H | 344–345 |
| (106) | H | $CH_3$ | 327–328 |
| (107) | $CH_3$ | $CH_3$ | 348–349 |
| (108) | $OCH_3$ | H | 315–316 |
| (109) | $C_6H_5$ | H | 297–298 |

EXAMPLE 2

2.65 g of 2-(p-tolyl)-5-t-butyl-benzoxazole of the formula

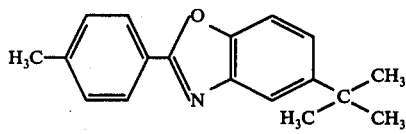

3.33 g of the Schiff's base obtained from 2-(p-formyl-phenyl)-s-triazolo[1,5-a]pyridine and o-chloroaniline, of the formula (101), and 2.5 g of potassium hydroxide powder having a water content of about 10% are stirred in 80 ml of dimethylformamide under nitrogen. The reaction mixture is warmed to 40° C. in the course of 15 minutes and is stirred for a further 1 hour at 40° to 45° C. The reaction mixture is worked up analogously to Example 1 and 3.55 g (75.5% of theory) of 4-[s-triazolo[1,5-a]pyrid-2-yl]-4'-(5-t-butyl-benzoxazol-2-yl)-stilbene of the formula

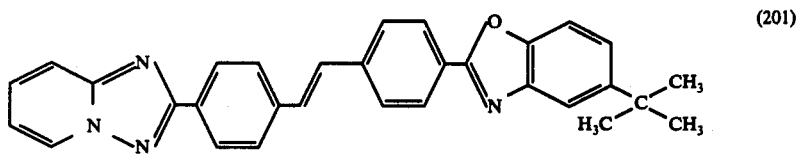

are obtained in the form of virtually colourless fine crystals which melt at 317° to 318° C. After recrystallisation from o-dichlorobenzene (bleaching earth) and then from dimethylformamide, 3.55 g (71.3% of theory) of pale greenish-tinged yellow small glossy, matted needles are obtained; the melting point is unchanged.

$C_{31}H_{26}N_4O$ (470.55): calculated: C 79.12 H 5.57 N 11.91%: found: C 79.30 H 5.75 N 12.01%.

The compounds of the formula

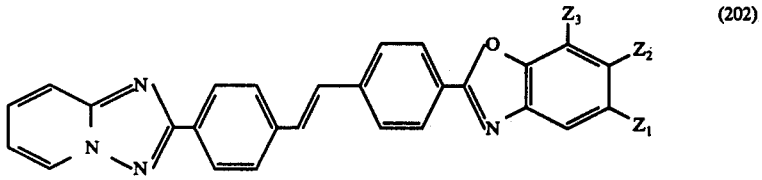

listed in Table II can be prepared in an analogous manner:

TABLE II

| No. | $Z_1$ | $Z_2$ | $Z_3$ | Melting point: °C |
|---|---|---|---|---|
| (203) | H | H | H | >360 |
| (204) | Cl | H | H | 342–343 |
| (205) | Cl | H | $CH_3$ | 309–310 |
| (206) | $CH_3$ | H | H | 324–325 |
| (207) | H | $CH_3$ | H | 322–323 |
| (208) | H | H | $CH_3$ | 286–287 |
| (209) | $CH_3$ | $CH_3$ | H | >360 |
| (210) | $CH_3$ | H | $CH_3$ | 275–276 |
| (211) | $CH_2$—$CH_2$—$CH_3$ | H | H | 273–274 |
| (212) | $CH(CH_3)_2$ | H | H | 269–270 |
| (213) | $C(CH_3)_3$ | H | $CH_3$ | 251–252 |
| (214) | $CH_3$ | H | $C(CH_3)_3$ | 303–304 |
| (215) | $CH_2C_6H_5$ | H | H | 296–297 |
| (216) | Cyclohexyl | H | H | 296–299 |
| (217) | $OCH_3$ | H | H | 272–273 |
| (218) | $C_6H_5$ | H | H | 327–328 |

TABLE II-continued

| No. | $Z_1$ | $Z_2$ | $Z_3$ | Melting point: °C |
|---|---|---|---|---|
| (219) | H | | $C_6H_5$ | H | 338–339 |

EXAMPLE 3

2.44 g of 2-(3-chloro-4-methylphenyl)-benzoxazole of the formula

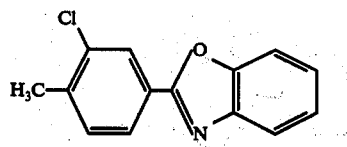

(300)

3.33 g of the Schiff's base obtained from 2-(p-formylphenyl)-s-triazolo[1,5-a]pyridine and o-chloroaniline, of the formula (101), and 2.5 g of potassium hydroxide powder having a water content of about 10% are stirred in 100 ml of dimethylformamide for 1 hour at 25° to 30° C. under nitrogen. The reaction mixture is worked up analogously to Example 1 and 4.1 g (91.5% of theory) of 4-[s-triazolo[1,5-a]pyrid-2-yl]-2'-chloro-4'-(benzoxazol-2-yl)-stilbene of the formula (301)

are obtained in the form of pale greenish-tinged yellow crystals which melt at 324° to 325° C. After recrystallisation from o-dichlorobenzene (bleaching earth) and then from dimethylformamide, 3.72 g (83.0% of theory) of small pale greenish-tinged yellow needles with a melting point of 330° to 331° C. are obtained.

$C_{27}H_{17}ClN_4O$ (448.91): calculated: C 72.24 H 3.82 N 12.48%: found: C 72.18 H 3.98 N 12.46%.

The compounds of the formula (302)

listed in Table III can be prepared in an analogous manner.

TABLE III

| No. | $R_3$ | $R_4$ | Melting point: °C |
|---|---|---|---|
| (303) | $CH_3$ | $CH_3$ | 318–319 |
| (304) | $C(CH_3)_3$ | H | 324–325 |
| (305) | H | $C_6H_5$ | 287–288 |

EXAMPLE 4

2.35 g of 3-phenyl-5-(p-tolyl)-isoxazole of the formula

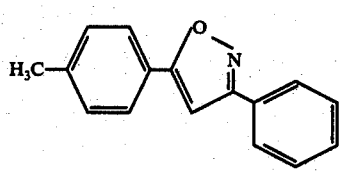

(400)

and 3.33 g of the Schiff's base obtained from 2-(p-formylphenyl)-s-triazolo[1,5-a]pyridine and o-chloroaniline, of the formula (101), are reacted in accordance with the instructions of Example 2. This gives 2.0 g (45.4% of theory) of 4-[s-triazolo[1,5-a]pyrid-2-yl]-4'-(3-phenyl-isoxazol-5-yl)-stilbene of the formula (401)

in the form of small pale beige, fine, matted needles with a melting point of 284° to 285° C. After recrystallising twice from xylene (bleaching earth), 1.75 g (39.8% of theory) of small, pale greenish-tinged yellow, matted needles are obtained. The melting point is unchanged.

$C_{29}H_{20}N_4O$ (440.48): calculated: C 79.07 H 4.58 N 12.72%: found: C 79.18 H 4.61 N 12.65%.

The compounds of the formula

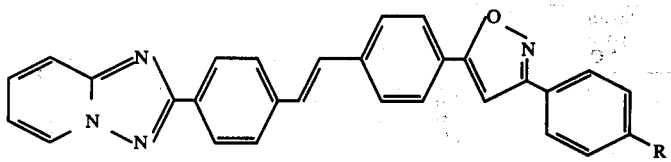

(402)

listed in Table IV can be prepared in an analogous manner.

TABLE IV

| No. | R | Melting point: °C |
|---|---|---|
| (403) | Cl | 275–276 |
| (404) | OCH₃ | 280–281 |
| (405) | C₆H₅ | 349–350 |

EXAMPLE 5

2.36 g of 3-phenyl-5-(p-tolyl)-1,2,4-oxadiazole of the formula

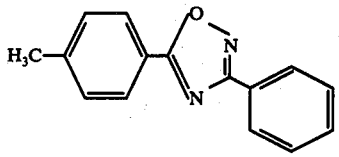

(500)

and 3.33 g of the Schiff's base obtained from 2-(p-formylphenyl)-s-triazolo[1,5-a]pyridine and o-chloroaniline, of the formula (101), are reacted in accordance with the instructions of Example 2. This gives 3.35 g (75.9% of theory) of 4-[s-triazolo[1,5-a]pyrid-2-yl]-4'-(3-phenyl-1,2,4-oxadiazol-5-yl)-stilbene of the formula

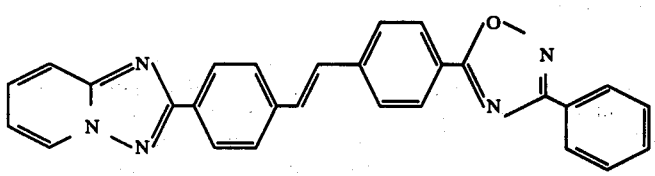

(501)

in the form of small, pale beige, matted needles with a melting point of 286° to 287° C. After recrystallisation from o-dichlorobenzene (bleaching earth) and then from dimethylformamide, 3.25 g (73.7% of theory) of small, pale green, matted needles with a melting point of 287°-to 288° C. are obtained.

$C_{28}H_{19}N_5O$ (441.47): calculated: C 76.17 H 4.34 N 15.87%: found: C 75.90 H 4.46 N 15.76%.

The compounds of the formula

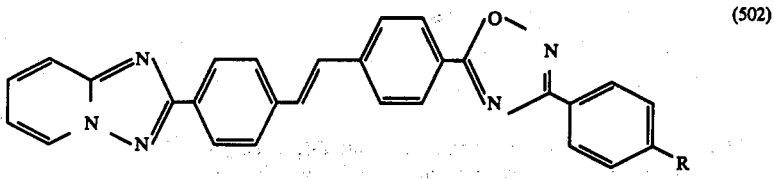

(502)

listed in Table V can be prepared in an analogous manner.

TABLE V

| No. | R | Melting point: °C |
|---|---|---|
| (503) | Cl | 286–287 |
| (504) | CH₃ | 259–260 |
| (505) | C(CH₃)₃ | 296–297 |
| (506) | OCH₃ | 274–275 |
| (507) | C₆H₅ | 287–288 |

EXAMPLE 6

2.36 g of 2-(p-tolyl)-5-phenyl-1,3,4-oxadiazole of the formula

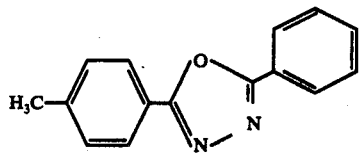

(600)

and 3.33 g of the Schiff's base obtained from 2-(p-formylphenyl)-s-triazolo[1,5-a]pyridine and o-chloroaniline of the formula (101), are reacted in accordance with the instructions of Example 2. This gives 3.37 g (76.4% of theory) of 4-[s-triazolo[1,5-a]pyrid-2-yl]-4'-(5-phenyl-1,3,4-oxadiazol-2-yl)-stilbene of the formula

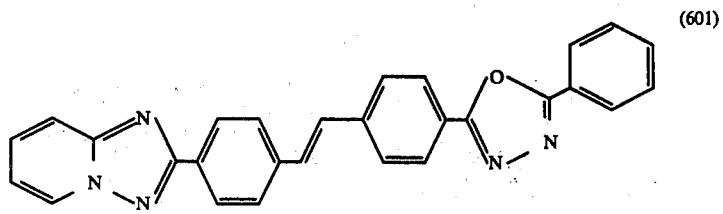

(601)

in the form of pale yellow fine crystals with a melting point of 279° to 280° C. After recrystallisation from o-dichlorobenzene (bleaching earth) and then from dimethylformamide, 2.85 g (64.6% of theory) of small greenish-tinged yellow fine needles are obtained, which melt at 280° to 281° C.

$C_{28}H_{19}N_5O$ (441.47): calculated: C 76.17 H 4.34 N 15.87%: found: C 76.36 H 4.56 N 15.85%.

The compounds of the formula

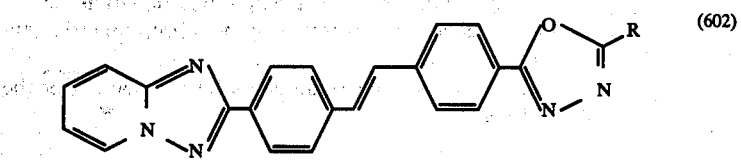
(602)

listed in Table VI can be prepared in an analogous manner.

chloro-4'-(5-phenyl-1,3,4-oxadiazol-2-yl)-stilbene of the formula

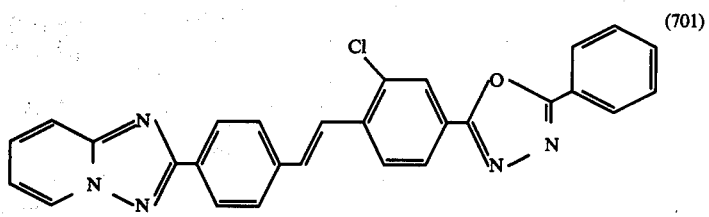
(701)

in the form of pale yellow fine crystals with a melting point of 312° to 313° C. After recrystallisation from o-dichlorobenzene (bleaching earth) and then from dimethylformamide, 4.09 g (86.1% of theory) of small, pale, greenish-tinged yellow, very fine needles are obtained, which melt at 322° to 323° C.

$C_{28}H_{18}ClN_5O$ (475.94): calculated: C 70.66 H 3.81 N 14.71%: found: C 70.45 H 3.99 N 14.83%.

The compounds of the formula

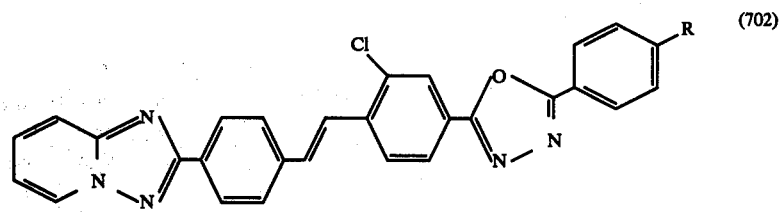
(702)

listed in Table VII can be prepared in an analogous manner.

TABLE VI

| No. | R | Melting point: °C |
|---|---|---|
| (603) | p-C$_6$H$_4$Cl | 322–323 |
| (604) | m-C$_6$H$_4$CH$_3$ | 267–268 |
| (605) | p-C$_6$H$_4$C(CH$_3$)$_3$ | 322–323 |
| (606) | o-C$_6$H$_4$OCH$_3$ | 283–284 |
| (607) | m-C$_6$H$_4$OCH$_3$ | 255–256 |
| (608) | p-C$_6$H$_4$OCH$_3$ | 277–278 |
| (609) | p-C$_6$H$_4$C$_6$H$_5$ | 323–324 |
| (610) | 1-Naphthyl | 282–283 |
| (611) | 2-Naphthyl | 296–297 |

TABLE VII

| No. | R | Melting point: °C |
|---|---|---|
| (703) | Cl | 347–348 |
| (704) | OCH$_3$ | 314–315 |
| (705) | C$_6$H$_5$ | 327–328 |

EXAMPLE 7

2.71 g of 2-(3-chloro-4-methylphenyl)-5-phenyl-1,3,4-oxadiazole of the formula

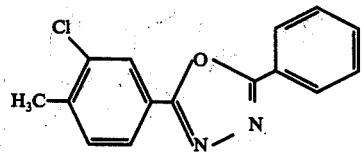
(700)

and 3.33 g of the Schiff's base obtained from 2-(p-formylphenyl)-s-triazolo[1,5-a]pyridine and o-chloroaniline, of the formula (101), are reacted in accordance with the instructions of Example 3. This gives 4.65 g (97.9% of theory) of 4-[s-triazolo[1,5-a]pyrid-2-yl]-2'-

The Schiff's base of 2-(p-formylphenyl)-s-triazolo[1,5-a]pyridine and o-chloroaniline, of the formula (101), can be prepared as follows from 2-(p-tolyl)-s-triazolo[1,5-a]-pyridine of the formula

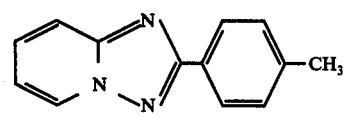
(26)

a) 2-(p-Bromomethyl-phenyl)-s-triazolo[1,5-a]pyridine (I):

41.85 g of 2-(p-tolyl)-s-triazolo[1,5-a]pyridine (26) are dissolved at 50° C. in 1,200 ml of dry carbon tetrachloride. 37.4 g of N-bromosuccinimide and 1 g of dibenzoyl peroxide are then added and the mixture is warmed gradually to the boil while stirring well and with exposure to a 400 W lamp. The reaction mixture is kept under reflux for 4 hours and is then cooled to 20° C. and the product which has precipitated is filtered off with suction. The succinimide is removed by washing with a large amount of water and the material on the suction filter is dried. This gives 39.2 g (58% of theory) of compound (I) in the form of a pale beige powder with a melting point of 192° to 193° C. After recrystallising twice from toluene, 32.3 g (56.1% of theory) of small, virtually colourless, glossy needles with a melting point of 195.5° to 196° C. are obtained.

b) 2-(p-Formylphenyl)-s-triazolo[1,5-a]-pyridine (II)

11.6 g of 2-nitropropane are introduced at about 30° C. into a solution of 2.3 g of sodium in 450 ml of absolute ethanol. The mixture is stirred for a further 1 hour and a solution of 28.8 g of 2-(p-bromomethyl-phenyl)-s-triazolo[1,5-a]pyridine (I) in 290 ml of dimethylformamide is now added. Subsequently, the reaction mixture is warmed to 50° C., then stirred for 20 hours without external warming and finally cooled to −10° C. The product which has precipitated is filtered off, washed with cold methanol and dried. This gives 19.3 g (86.5% of theory) of compound (II) in the form of a pale yellow powder with a melting point of 243° to 244° C. After recrystallising twice from dimethylformamide, 14.67 g (65.7% of theory) of small, virtually colourless, glossy needles with a melting point of 246° to 247° C. are obtained.

c) 2-[4-(o-Chlorophenylimino-methyl)-phenyl]-s-triazolo[1,5-a]pyridine (101)

22.32 g of 2-(p-formylphenyl)-s-triazolo[1,5-a]pyridine (II), 14.03 g of o-chloroaniline and 1 g of boric acid in 350 ml of xylene are refluxed for 2 hours, the water formed being distilled off. The mixture is cooled to 60° C., 450 ml of methanol are added and the resulting mixture is further cooled to −10° C. The product which has precipitated is filtered off with suction, washed with 100 ml of cold methanol and dried. This gives 26.3 g (79.1% of theory) of compound (101) in the form of a pale beige powder with a melting point of 135° to 136° C. After recrystallising twice from methanol, 22.2 g (66.7% of theory) of small, pale yellow, glossy needles with a melting point of 135° to 136° C. are obtained.

EXAMPLE 8

A polyester fabric (for example "Dacron") is padded at room temperature (about 20° C. with an aqueous dispersion which contains, per litre, 2 g of one of the compounds of the formulae (201), (208), (210), (401), (501) or (601) and 1 g of an addition product of about 8 mols of ethylene oxide and 1 mol of p-tert. octylphenol and is dried at about 100° C. The dry material is then subjected to a heat treatment at 170° to 220° C. and this treatment takes from 2 minutes to several seconds, depending on the temperature. The material treated in this way has a considerably whiter appearance than the untreated material.

EXAMPLE 9

100 parts of polyester granules of terephthalic acid ethylene glycol polyester are intimately mixed with 0.05 part of one of the compounds of the formulae (201) or (203) to (219) and the mixture is melted at 285° C., with stirring. After the spinning melt has been spun out through conventional spinnerets, highly brightened polyester fibres with good fastness to light are obtained.

It is also possible to add the compounds mentioned above to the starting materials before or during the polycondensation reaction which gives the polyester.

What is claimed is:

1. A stilbene compound of the formula

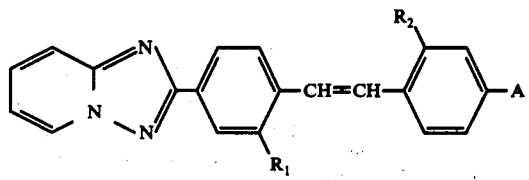

in which $R_1$ and $R_2$ independently of one another are hydrogen or chlorine and A is a mono-nuclear or polynuclear aromatic heterocyclic structure which contains oxygen atoms or oxygen and nitrogen atoms and is unsubstituted or substituted by nonchromophoric substituents.

2. A stilbene compound according to claim 1 of the formula

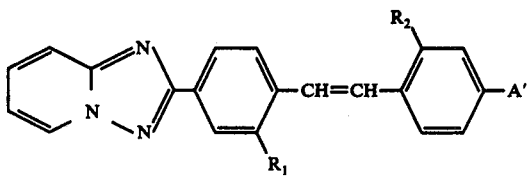

in which $R_1$ and $R_2$ independently of one another are hydrogen or chlorine and A' is a benzo[b]furan-2-yl, benzoxazol-2-yl, 3-phenyl-isoxazol-5-yl, 3-phenyl-1,2,4-oxadiazol-5-yl, 5-phenyl-1,3,4-oxadiazol-2-yl, 5-(1-naphthyl)-1,3,4-oxadiazol-2-yl or 5-(2-naphthyl)-1,3,4-oxadiazol-2-yl radical which is unsubstituted or substituted by non-chromophoric substituents.

3. A stilbene compound according to claim 2, of the formula

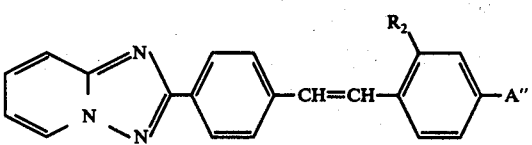

in which $R_2$ is hydrogen or chlorine and A" is a radical of the formula

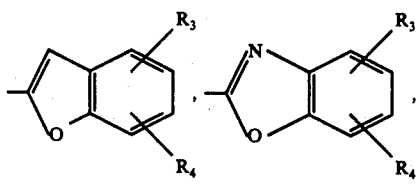

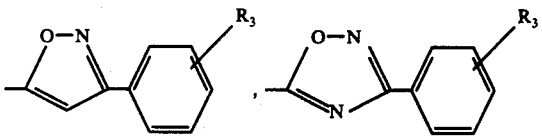

-continued

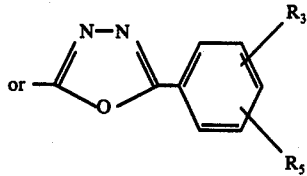

in which $R_3$ is hydrogen, halogen, alkyl having 1 to 4 C atoms, alkoxy having 1 to 4 C atoms, cyclohexyl, phenyl or phenylalkyl having 1 to 4 C atoms in the alkyl part, or $R_3$ together with $R_5$ is the complement to a 1-naphthyl or 2-naphthyl radical, $R_4$ is hydrogen or alkyl having 1 to 4 C atoms and $R_5$ is hydrogen or, together with $R_3$, is the complement to a 1-naphthyl or 2-naphthyl radical.

4. A stilbene compound according to claim 3, of the formula

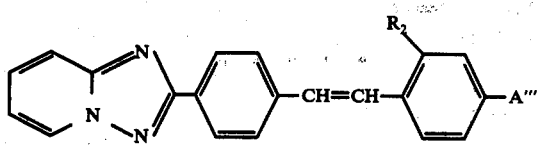

in which $R_2$ is hydrogen or chlorine and A''' is a radical of the formula

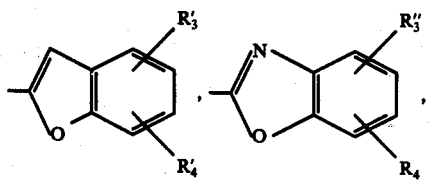

-continued

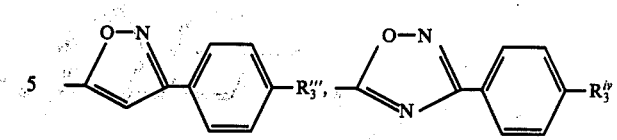

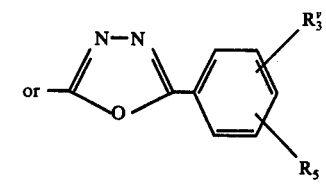

in which $R_3'$ is hydrogen, chlorine, methyl, methoxy or phenyl, $R_4'$ is hydrogen or methyl, $R_3''$ is hydrogen, chlorine, alkyl having 1 to 4 C atoms, methoxy, phenyl, benzyl or cyclohexyl, $R_4$ is hydrogen or alkyl having 1 to 4 C atoms, $R_3'''$ is hydrogen, chlorine, methoxy or phenyl, $R_3^{iv}$ is hydrogen, chlorine, methoxy, alkyl having 1 to 4 C atoms or phenyl, $R_3^v$ is hydrogen, chlorine, alkyl having 1 to 4 C atoms, methoxy or phenyl or, together with $R_5$ is the complement to a 1-naphthyl or 2-naphthyl radical, and $R_5$ is hydrogen or, together with $R_3'$, is the complement to a 1-naphthyl or 2-naphthyl radical.

5. The stilbene compound according to claim 3, of the formula

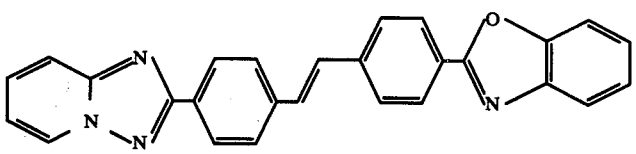

6. The stilbene compound according to claim 3, of the formula

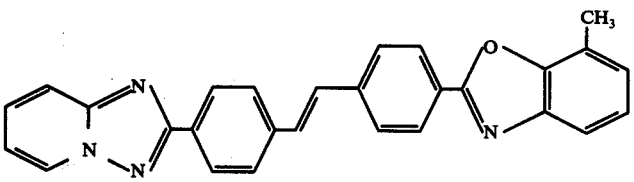

7. The stilbene compound according to claim 3, of the formula

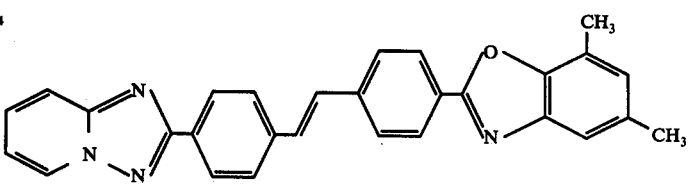

8. The stilbene compound according to claim 3, of the formula

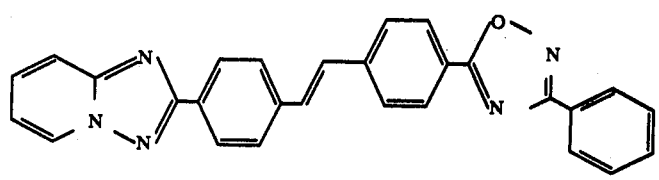
9. The stilbene compound according to claim 3, of the formula
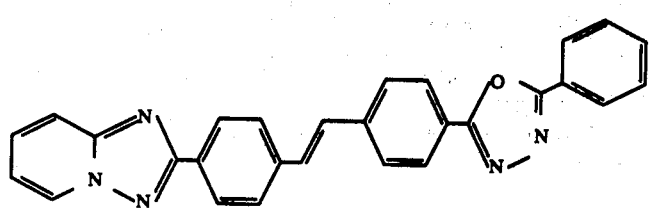
* * * * *